United States Patent [19]
Peters

[11] Patent Number: 5,441,485
[45] Date of Patent: Aug. 15, 1995

[54] BLADDER CATHETER

[76] Inventor: Michael J. Peters, 2196 Wycliffe, West Bloomfield, Mich. 48323

[21] Appl. No.: 201,274

[22] Filed: Feb. 24, 1994

[51] Int. Cl.⁶ .......................................... A61M 25/14
[52] U.S. Cl. ................................... 604/101; 606/192
[58] Field of Search ............... 604/96, 97, 101, 98, 604/99, 100, 102, 103; 606/192–196

[56] References Cited

U.S. PATENT DOCUMENTS

| | | | |
|---|---|---|---|
| 2,687,131 | 8/1954 | Raichie | 604/101 |
| 2,849,002 | 8/1958 | Oddo | 604/101 |
| 3,084,693 | 4/1963 | Cathcart | 128/349 |
| 3,421,509 | 1/1969 | Fiore | 128/349 |
| 3,592,197 | 7/1971 | Cohen | 128/349 |
| 3,811,448 | 5/1974 | Morton | 128/349 |
| 3,954,110 | 5/1976 | Hutchison | 128/349 |
| 4,043,346 | 8/1977 | Mobley et al. | 128/349 |
| 4,217,903 | 8/1980 | Witherow | 128/349 |
| 4,266,999 | 5/1981 | Baier | 156/227 |
| 4,349,029 | 9/1982 | Mott | 128/349 |
| 4,630,609 | 12/1986 | Chin | 604/101 |
| 4,820,270 | 4/1989 | Hardcastle et al. | 604/96 |
| 4,983,165 | 1/1991 | Loiterman | 604/101 |
| 4,995,868 | 2/1991 | Brazier | 604/105 |
| 5,019,042 | 5/1991 | Sahota | 604/101 |
| 5,062,425 | 11/1991 | Tucker | 604/97 |
| 5,213,577 | 5/1993 | Kratzer | 604/101 |
| 5,342,306 | 8/1994 | Michael | 604/101 |

FOREIGN PATENT DOCUMENTS

| | | | |
|---|---|---|---|
| 511951 | 6/1976 | U.S.S.R. | 604/101 |

*Primary Examiner*—Paul J. Hirsch
*Attorney, Agent, or Firm*—Lyman R. Lyon

[57] ABSTRACT

A catheter comprises a relatively stiff drainage tube having an inflatable sheath telescoped thereover. The sheath is inflated after insertion of the tube and sheath into the urethra of a patient. The sheath has a plurality of circumferentially spaced relative thin sections that form circumferentially spaced catheter retention balloons at the insertion end of said tube when said sheath is inflated thereby to facilitate complete drainage of the bladder.

3 Claims, 2 Drawing Sheets

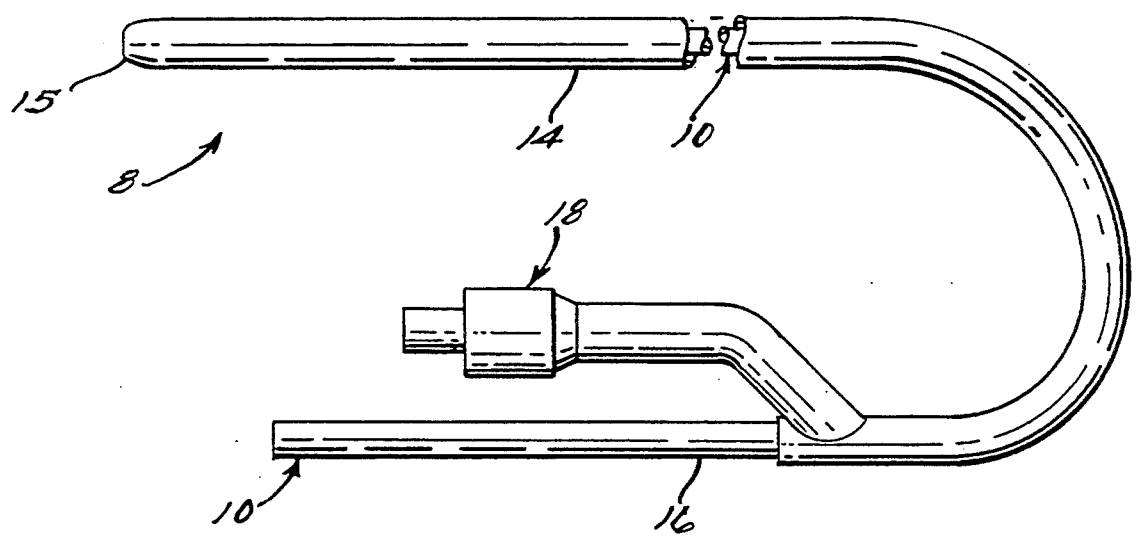
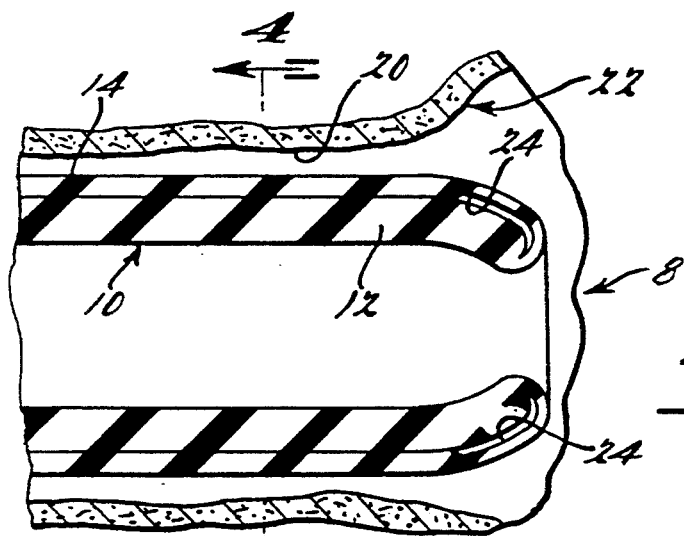
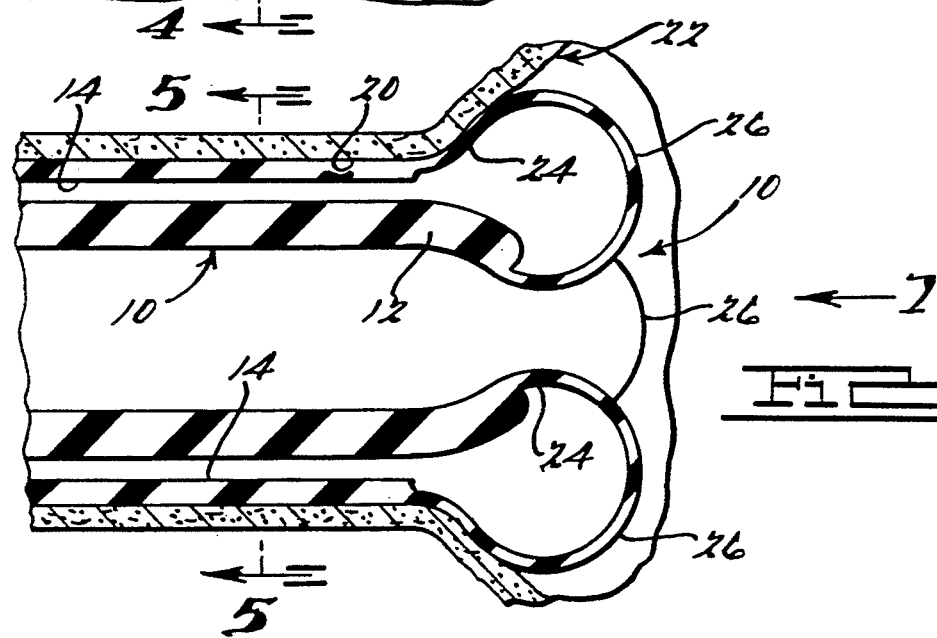

BLADDER CATHETER

BACKGROUND OF THE INVENTION

This invention relates generally to catheters and more specifically to a catheter for draining urine from the human bladder.

A bladder catheter is a long tubular device which is inserted through the human urethra into the bladder to drain urine. In order to prevent the catheter from being inadvertently withdrawn from the bladder, one commonly used catheter utilizes an inflatable balloon which surrounds the tube near the insertion end just behind the drainage opening. After passing through the urethra, the balloon is inflated around the tube and rests on the wall of the bladder about the urethral opening, so as to retain the end of the catheter and the drainage opening therein inside the bladder. The balloon is deflated before withdrawing the catheter from the bladder.

One problem with such known catheters is that the drainage opening of the catheter is forward of the balloon. Therefore, the drainage openings do not drain urine which collects below the openings. This residual urine increases the chance of infection by providing a pool in which bacteria introduced into the bladder may grow.

Another problem with known catheters is the need to stock a large supply of different sizes. Currently, a catheter must be chosen for each patient having a diameter sufficiently large to seal the urethra to prevent urine leakage, but sufficiently small enough in diameter to pass through the urethra. As a result, most hospitals now carry approximately ten sizes of bladder catheters.

Another problem with commonly-used catheters is discomfort suffered by the patient during insertion of the catheter. The larger the diameter of the catheter, the more discomfort will be suffered by the patient incident to insertion through the urethra. The source of discomfort is that a large diameter catheter is required to seal against urine leakage. As previously discussed, in order to prevent urine leakage, a catheter with a diameter large enough to seal the urethra must be chosen. Any increase in the diameter of the catheter to effect sealing increases the discomfort suffered by the patient during insertion of the catheter through the urethra, as well as increased damage to the urethral lining.

Yet another problem exhibited by commonly-used catheters alluded to above, is discomfort suffered by the patient while the catheter is in place. The catheters are relatively stiff in order to facilitate insertion, and they do not conform to the individual patient's anatomy. The size and stiffness of the catheter inserted into the urethra, which is not perfectly tubular, forces the patient's urethra to conform to the catheter and causes discomfort to the patient while the catheter is in place.

SUMMARY OF THE INVENTION

The aforementioned problems are solved, in accordance with a preferred constructed embodiment of the present invention, by a catheter having an inflatable outer sheath made from, for example, latex. Circumferentially spaced sections of the sheath are of reduced thickness so as to facilitate inflation of a plurality of circumferentially spaced retention balloons at the insertion end of the catheter.

The preferred embodiment of the catheter includes a relatively thin-walled rigid tube which is the main drainage passageway for urine from the body. The tube is surrounded by the inflatable sheath which is sealed at both ends of the tube. The sheath can be inflated by, for example, a standard water injector valve at the outer end of the catheter.

When the relatively thin sheath is inflated, it expands to seal the urethra while conforming to the individual patient's anatomy. Because the inflatable sheath is expanded to seal the urethra after insertion, the diameter of the catheter during insertion can be minimized which makes it easier to insert and much more comfortable and therefore less traumatic to the patient. In addition, the catheter is more comfortable while in place because of the formfitting, flexible, outer inflatable sheath. Furthermore, because the catheter is inflated to conform to the anatomy of each individual patient, one minimum-diameter catheter will fit most patients, reducing the need to stock many different-sized catheters.

The circumferentially spaced sections of the inflatable sheath of reduced thickness at the insertion end of the catheter cause selective ballooning of the inflatable sheath, creating retention balloons. The retention balloons keep the catheter from being inadvertently withdrawn but do not increase the diameter of the catheter when uninflated. In accordance with a feature of the instant invention, circumferential spacing of the retention balloons permits drainage from the lowermost point of the bladder, which facilitates substantially complete drainage of urine from the bladder, reducing the possibility of infection.

BRIEF DESCRIPTION OF THE DRAWINGS

FIG. 1 is an elevational view of the preferred embodiment of the catheter in an uninflated state;

FIG. 2 is a cross-sectional view of the insertion end of the catheter of FIG. 1 disposed within the urethra and penetrating the bladder but prior to inflation;

FIG. 3 is a cross-sectional view of the insertion end of the catheter of FIG. 2 after inflation;

DETAILED DESCRIPTION OF THE PREFERRED EMBODIMENT

Figure 4:
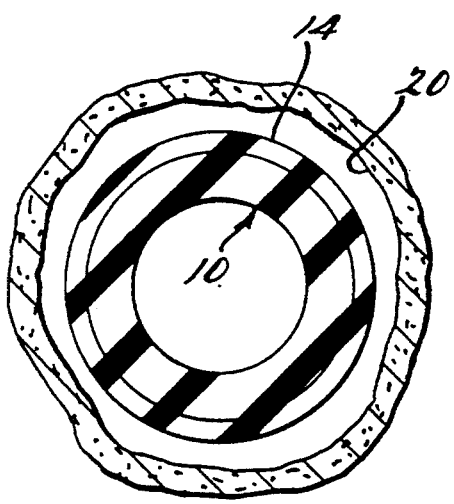
FIG. 4 is a cross-sectional view of the uninflated catheter taken along line 4—4 of FIG. 2.
Figure 5:
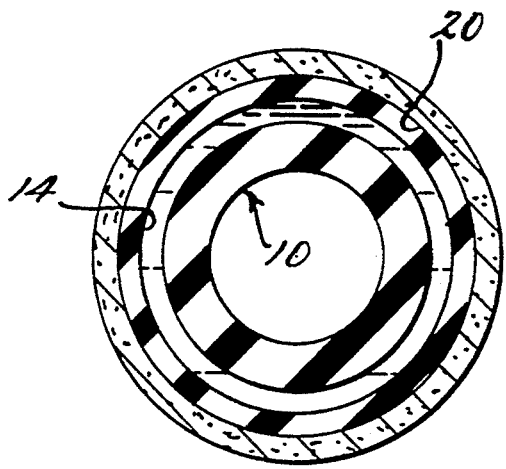
FIG. 5 is a cross-sectional view of the catheter of FIG. 4 taken along line 5—5 of FIG. 3.

In accordance With a preferred constructed embodiment of the invention, a tubular catheter 8 comprises a relatively stiff tube 10 that provides a drainage passageway for urine from the bladder. The tube 10 has an insertion end 12 that is surrounded by a relatively thin flexible inflatable sheath or membrane 14 which is preferably integral with the tube 10. The sheath 14 is reentrantly folded back over the insertion end 12 of the tube 10. The inflatable sheath 14 is sealed to an outer end 16 of the tube 10.

As seen in FIG. 1, a conventional water or air injector valve 18 is connected to the sheath 14 for the injection of water or air, between the drainage tube 10 and sheath 14. The catheter 8 is of minimum diameter when uninflated so that it is easily inserted through a patient's urethra 20 and into the bladder 22, as shown in FIG. 3.

Figure 7:
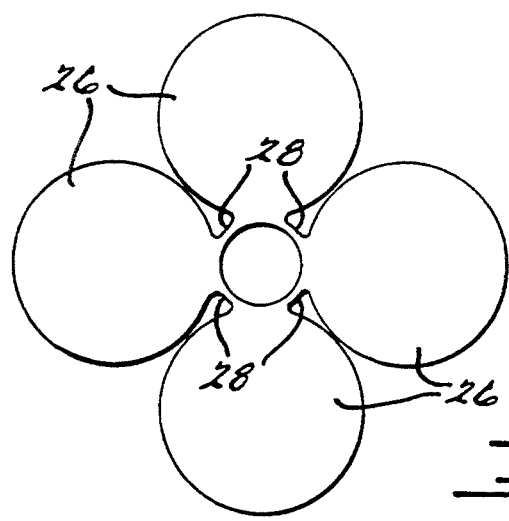
FIG. 7 is a view of the catheter taken in the direction of the arrow 7 of FIG. 3.

When the sheath 14 is inflated, as shown in FIGS. 3 and 7, it expands to conform to the individual patient's anatomy and seal the urethra 20 against the passage of fluid.

In accordance with one feature of the present invention, a plurality of relatively thin, circumferentially spaced expandable sections 24 are formed in the sheath 14 at the insertion end 12 thereof which cause selective ballooning of the inflatable sheath 14 to create a plurality of circumferentially spaced catheter retention balloons 26. As seen in FIG. 2, the uninflated sections 24 of the sheath 14 at the tip of the tube portion 10 of the catheter 8 do not impede insertion of the catheter 8. Upon inflation of the sheath 14, the sections 24 form the balloons 26.

FIG. 4 shows the balloons 26 after inflation. The retention balloons 26 preclude inadvertent withdrawal of the catheter 8 from the bladder 22. In, accordance with the present invention, as best seen in. FIG. 7, circumferentially spaced drainage canals 28 open directly into the tube 10 adjacent the wall of the bladder 22, due to the circumferentially spaced relation of the balloons. 26 allowing for complete drainage of urine, from the bladder 22.

Figure 6:
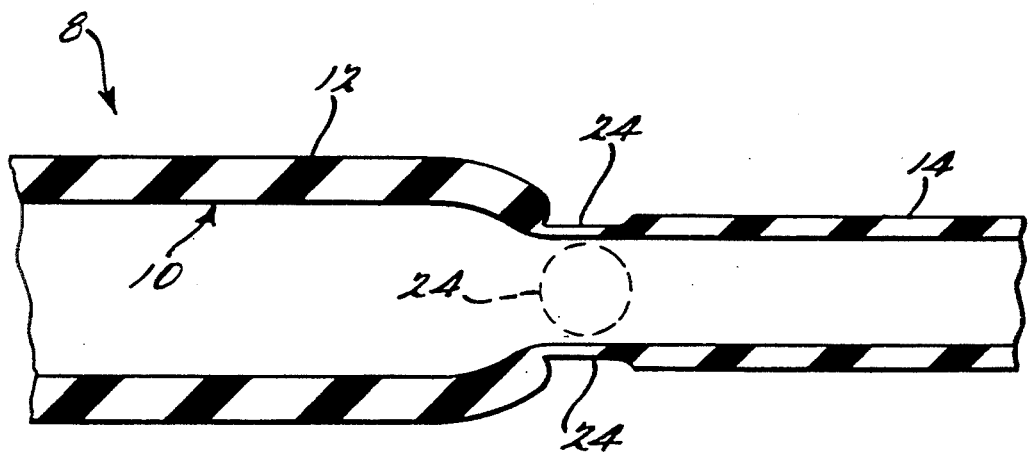
FIG. 6 illustrates the catheter of FIG. 1 at one stage of manufacture thereof.

As shown in FIG. 6, the catheter 8 is preferably molded as a single tube having a wall portions of different thickness to form the relatively stiff drainage tube 10, the relatively flexible inflatable sheath 14, and the thin, very flexible sections 24 that inflate to form the retention balloons 26. These three sections of different stiffness can be obtained by varying the thickness of the walls of the catheter 8, by molding the three sections in different durometers, or by a combination of the thickness and durometer variables. After the catheter 8 is cast, the inflatable sheath 14 including the four balloon-forming panels 24 are reentrantly folded back over the insertion end 12 of the tube catheter 10 and sealed to the outer end 16 of the tube 10.

While the preferred embodiment of the invention has been disclosed, it should be appreciated that the invention is susceptible of modification without departing from the scope of the following claims.

I claim:

1. A catheter comprising:
   a relatively stiff tube having an insertion end for insertion into the urethra of a patient and an opposite end;
   an inflatable sheath telescoped over said tube and sealed thereto at both the insertion end and the opposite end of said tube;
   means at the opposite end of said catheter for inflating said sheath after insertion of said catheter into the urethra of a patient; and
   a plurality of circumferentially spaced sections of reduced thickness at the insertion end thereof that are inflatable to define circumferentially spaced retention balloons when said sheath is inflated.

2. The catheter of claim 1 wherein said tube, sheath and reduced sections are integral and said sheath is reentrantly folded over said tube.

3. The catheter of claim 1 wherein said means comprises a water pump.

* * * * *